(12) United States Patent
Sabelle et al.

(10) Patent No.: US 8,551,189 B2
(45) Date of Patent: Oct. 8, 2013

(54) COMPOSITION COMPRISING AT LEAST ONE 1,8-DIHYDROXYNAPHTHALENE DERIVATIVE AND AT LEAST ONE BASIFYING AGENT DIFFERENT FROM AQUEOUS AMMONIA, PROCESS FOR DYEING KERATIN FIBRES USING THE COMPOSITION

(71) Applicant: L'Oreal, Paris (FR)

(72) Inventors: Stephane Sabelle, Paris (FR); Christophe Rondot, Mitry-Mory (FR); Karine Picolet, Verrieres-le-Buisson (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/710,333

(22) Filed: Dec. 10, 2012

(65) Prior Publication Data

US 2013/0219633 A1    Aug. 29, 2013

Related U.S. Application Data

(63) Continuation of application No. 13/502,257, filed as application No. PCT/EP2010/065484 on Oct. 14, 2010, now abandoned.

(60) Provisional application No. 61/253,167, filed on Oct. 20, 2009.

(30) Foreign Application Priority Data

Oct. 16, 2009   (FR) ...................................... 09 57282

(51) Int. Cl.
*A61Q 5/10*      (2006.01)

(52) U.S. Cl.
USPC .................... 8/405; 8/407; 132/202; 132/208

(58) Field of Classification Search
USPC ............................... 8/405, 407; 132/202, 208
See application file for complete search history.

(56) References Cited

U.S. PATENT DOCUMENTS 5,873,910 A * 2/1999 Henrion et al. ................... 8/406

FOREIGN PATENT DOCUMENTS

FR          2793408      * 11/2000

OTHER PUBLICATIONS

STIC Search Report dated Jun. 13, 2013.*

* cited by examiner

*Primary Examiner* — Eisa Elhilo
(74) *Attorney, Agent, or Firm* — O'Brien Jones, PLLC

(57) ABSTRACT

The subject of the invention is a composition for dyeing keratin fibers, comprising at least one 1,8-dihydroxynaphthalene derivative and at least one basifying agent other than aqueous ammonia; the use of the composition for hair dyeing and also the use of the composition in a dyeing process for keratin fibers. The composition according to the invention makes it possible to dye keratin fibers under mild oxidizing conditions even without using an oxidation base and an aromatic amine, while at the same time covering a broad color range with 1,8-dihydroxynaphthalene derivatives. The observed dyeing under oxidizing conditions operates under mild conditions of oxidation and/or basifying agent, in particular in the air, and does not produce any unpleasant odor.

21 Claims, No Drawings

COMPOSITION COMPRISING AT LEAST ONE 1,8-DIHYDROXYNAPHTHALENE DERIVATIVE AND AT LEAST ONE BASIFYING AGENT DIFFERENT FROM AQUEOUS AMMONIA, PROCESS FOR DYEING KERATIN FIBRES USING THE COMPOSITION

This is a continuation of application Ser. No. 13/502,257, filed Dec. 10, 2012 now abandoned, which claims priority to PCT/EP2010/065484, filed Oct. 14, 2010, French Application No. 0957282, filed Oct. 16, 2009, and U.S. Provisional Application No. 61/253,167, filed on Oct. 20, 2009, all of which are incorporated herein by reference.

A subject of the invention is a composition for dyeing keratin fibres, comprising at least one 1,8-dihydroxynaphthalene derivative and at least one basifying agent other than aqueous ammonia; the use of the composition for hair dyeing and also the use of the composition in a dyeing process.

It is known practice to obtain "permanent" colourings with dyeing compositions containing oxidation dye precursors, generally known as oxidation bases, such as ortho- or para-phenylenediamines, ortho- or para-aminophenols and heterocyclic compounds. These oxidation bases are colourless or weakly coloured compounds which, in combination with oxidizing products, can give rise, by means of an oxidative condensation process, to coloured compounds. It is also known that it is possible to vary the shades obtained by combining these oxidation bases with couplers or colouring modifiers, the latter being chosen in particular from aromatic meta-diamines, meta-aminophenols, meta-diphenols and certain heterocyclic compounds, such as indole compounds. This oxidation dyeing process consists in applying, to the keratin fibres, bases or a mixture of bases and of couplers with hydrogen peroxide ($H_2O_2$ or aqueous hydrogen peroxide solution) as oxidizing agent, in allowing to diffuse and then in rinsing the fibres. The colourings which result therefrom are permanent, powerful and resistant to external agents, in particular to light, bad weather, washing, perspiration and rubbing actions.

The oxidation bases and the oxidation couplers make it possible to obtain a rich range of colours, but they generally require the presence i) of an aromatic amine, ii) of hydrogen peroxide as oxidizing agent, or iii) of aqueous ammonia, thus leading to unpleasant aspects associated with the odour of the aqueous ammonia and fibre damage associated with the presence of hydrogen peroxide.

In addition, drawbacks such as staining and problems of discomfort can be encountered with oxidation dyeing.

1,8-Dihydroxynaphthalene derivatives optionally substituted with chlorine or bromine atoms have been used in oxidation dyeing of the hair (WO 94/18937). However, the processes described require in particular the use of aqueous ammonia in large amounts, which has the effect of generating a very unpleasant odour. In addition, when the 1,8-dihydroxynaphthalene derivatives are applied in the absence of aqueous ammonia, the dyeing can become less resistant to shampooings. It is also, in general, very difficult to succeed in bringing out the oxidation precursors in the absence of aqueous ammonia, such that the colourings obtained are much duller and less powerful.

There is therefore a real need to perform dyeing using 1,8-dihydroxynaphthalene that may be of natural origin, under milder conditions, with reduced keratin fibre damage or even no fibre damage, while at the same time providing colourings which withstand external agents (light, bad weather, shampooing), and which are persistent, homogeneous, powerful and chromatic, if possible with no unpleasant odour, or a very reduced one, linked to the treatment of the hair.

This aim is achieved by the present invention, the subject of which is a process for dyeing keratin fibres, in particular the hair, by treating said fibres with:

i) one or more 1,8-dihydroxynaphthalene derivative(s) of formula (I):

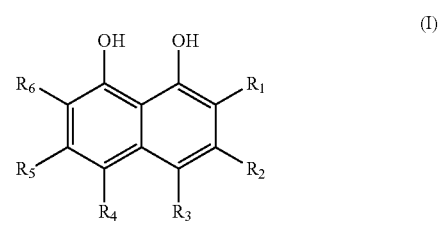

its of inorganic or organic acids or bases, its optical isomers, geometric isomers, its tautomers, and/or its solvates such as the hydrates; in which formula (I):

$R_1$ and $R_6$ represent, independently of one another:
a hydrogen atom,
a $C_1$-$C_4$ alkyl radical which can be functionalized with one or more hydroxyl or ($C_1$-$C_4$)alkoxycarbonyl radicals,
a carboxylic radical —$CO_2H$,
a ($C_1$-$C_4$)alkoxycarbonyl radical,
a ($C_1$-$C_4$)alkylcarbonyl radical which can be functionalized with a ($C_1$-$C_4$)alkylcarbonyl radical or a ($C_1$-$C_4$) alkoxycarbonyl radical,
a $C_1$-$C_4$ alkoxy radical,
a carboxaldehyde radical —CHO,
a sulphonic radical —$SO_3H$;

$R_2$ and $R_5$ represent, independently of one another:
a hydrogen atom,
a hydroxyl radical,
a $C_1$-$C_4$ alkyl radical which can be functionalized with one or more hydroxyl or ($C_1$-$C_4$)alkoxycarbonyl radicals,
a carboxylic radical —$CO_2H$,
a ($C_1$-$C_4$)alkoxycarbonyl radical,
a ($C_1$-$C_4$)alkylcarbonyl radical which can be functionalized with a hydroxyl radical,
a $C_1$-$C_4$ alkoxy radical,
a carboxaldehyde radical —CHO,
a sulphonic radical —$SO_3H$;

$R_3$ and $R_4$ represent, independently of one another:
a hydrogen atom,
a hydroxyl radical,
a $C_1$-$C_4$ alkyl radical which can be functionalized with one or more hydroxyl or ($C_1$-$C_4$)alkoxycarbonyl radicals,
a carboxylic radical —$CO_2H$,
a ($C_1$-$C_4$)alkoxycarbonyl radical,
a ($C_1$-$C_4$)alkylcarbonyl radical which can be functionalized with a ($C_1$-$C_4$)alkylcarbonyl radical or a ($C_1$-$C_4$) alkoxycarbonyl radical;

$R_1$ and $R_2$ can form, together with the carbon atoms to which they are attached, a heterocycle optionally substituted with an oxo group, such as pyrone, particularly 4-pyrone, which can be functionalized with one or two $C_1$-$C_4$ alkyl radical(s):

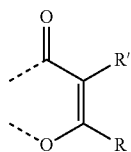

with R and R', which may be identical or different, representing a hydrogen atom or a $C_1$-$C_4$ alkyl radical; preferably, R and R' represent a hydrogen atom or R' represents a hydrogen atom and R represents a $C_1$-$C_4$ alkyl radical; and ii) one or more basifying agent(s) other than aqueous ammonia;

it being understood that:

the 1,8-dihydroxynaphthalene derivative(s) of formula (I) and the basifying agent(s) can be applied simultaneously or successively to the keratin fibres, and the dyeing process does not involve aqueous ammonia.

Another subject of the invention relates to the use of compounds of formula (I) as defined above, for dyeing keratin fibres, in particular human keratin fibres such as the hair.

Another subject of the invention relates to a cosmetic composition which contains:

i) one or more 1,8-dihydroxynaphthalene derivatives of formula (I) as described above; and ii) one or more basifying agent(s) other than aqueous ammonia; with the proviso that 1,8-dihydroxynaphthalene derivative(s) of formula (I) cannot represent:

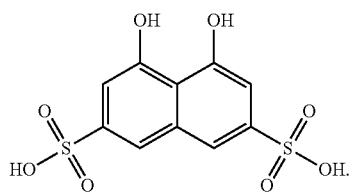 [SMILES: O=S(=O)(O)c1cc(O)c2c(O)cc(S(=O)(=O)O)cc2c1]

Another subject of the invention relates to a device comprising from 2 to 5 compartments containing from 2 to 5 compositions, in which the following ingredients are distributed:

i) one or more 1,8-dihydroxynaphthalene derivative(s) of formula (I) as defined above, ii) one or more basifying agent(s) other than aqueous ammonia, and iii) optionally, one or more chemical oxidizing agent(s) and/or iv) one or more oxidation catalysts, and v) optionally, one or more mordant(s).

The composition according to the invention makes it possible to dye the keratin fibres under mild conditions, while covering a broad colour range.

In addition, the composition according to the invention has the advantage of dyeing human keratin fibres with resulting colourings which are powerful, chromatic and resistant to washing, perspiration, sebum and light, without impairing said fibres. The colourings obtained using the process also give colours which are homogeneous from the root to the end of a fibre (a low colouring selectivity). There is no unpleasant odour associated with the dyeing process according to the invention to be deplored, as can occur with the use of a basifying agent such as aqueous ammonia.

For the purpose of the present invention, and unless otherwise indicated:

The alkyl radicals are linear or branched, saturated, generally $C_1$-$C_4$, hydrocarbon-based radicals such as methyl, ethyl, propyl and butyl.

The "alkylene" radicals are divalent saturated, linear or branched hydrocarbon radicals, generally $C_1$-$C_{10}$, preferably ($C_2$-$C_6$)alkylene, such as ethylene, propylene and butylene;

the latter being optionally interrupted by one or more heteroatoms and/or being optionally substituted such as:
(A) —$(CR'R''_2)_n$—X—$(CR'R''_2)_p$— or (B) —$(CR'R''_2)_n$—X—$(CR'R''_2)_p$—Y—$(CR'R''_2)_q$— wherein n, p and q, identical or different, each representing an integer between 1 to 4; with in (A) n+p representing an integer between 2 and 6 or (B) n+p+q representing an integer between 3 and 6;

X and Y, identical or different, represent a bond, an heteroatom such as oxygen atom or NR with R representing an hydrogen atom, or (hydroxyl)($C_1$-$C_6$)alkyl group, preferably X=Y; and R' and R'', identical or different, represent an hydrogen atom or a group selected from hydroxyl and ($C_1$-$C_6$) alkyl such as methyl;

preferably alkylene radical represents (A) with more particularly R' and R'' representing an hydrogen atom.

The alkoxy radicals are alkyloxy radicals, with alkyl as defined above, preferably $C_1$-$C_4$, such as methoxy, ethoxy, propoxy and butoxy.

The heterocycle optionally substituted with an oxo group is a heterocycle fused to the 1,8-dihydroxynaphthalene nucleus via the $R_1$ and $R_2$ radicals; said heterocycle comprising from 5 to 7 ring members, from one to three heteroatoms chosen from oxygen, sulphur or nitrogen atoms, and which may also comprise an oxo or carbonyl group, and an unsaturation preferably conjugated with the oxo group.

The term "mild conditions" is intended to mean without the simultaneous use, in the process or in the composition according to the invention, of a chemical oxidizing agent other than air, of a high amount of basifying agent having an unpleasant odour and of the presence of an oxidation base and of couplers of aromatic amine type. The process of the invention is carried out under mild conditions, i.e. the composition applied to the hair according to the invention does not contain aqueous ammonia. The composition comprises a basifying agent which does not exhibit any problem regarding odour, and a low amount of or even no chemical oxidizing agent and a low amount of or even no oxidization bases and couplers derived from an aromatic amine.

For the notion of "chemical oxidizing agents", see "oxidizing agents and oxidation catalysts" hereinafter.

1,8-dihydroxynaphthalene derivative of formula (I)

One particular embodiment of the invention relates to 1,8-dihydroxynaphthalene derivatives of formula (I) for which $R_1$ and $R_6$ represent, independently of one another:

a hydrogen atom, a $C_1$-$C_4$ alkyl radical, a carboxylic radical —$CO_2H$, a ($C_1$-$C_4$)alkoxycarbonyl radical, a ($C_1$-$C_4$)alkylcarbonyl radical which can be functionalized with a ($C_1$-$C_4$)alkylcarbonyl radical or a ($C_1$-$C_4$) alkoxycarbonyl radical;

more particularly, $R_1$ and $R_6$ represent, independently of one another:

a hydrogen atom, a $C_1$-$C_4$ alkyl radical, a ($C_1$-$C_4$)alkoxycarbonyl radical, a ($C_1$-$C_4$)alkylcarbonyl radical which can be functionalized with a ($C_1$-$C_4$)alkylcarbonyl radical or a ($C_1$-$C_4$) alkoxycarbonyl radical.

According to another particular embodiment of the invention, the 1,8-dihydroxynaphthalene derivatives of formula (I) are such that $R_2$ and $R_5$ represent, independently of one another:

a hydrogen atom, a hydroxyl radical, a $C_1$-$C_4$ alkyl radical which can be functionalized with a ($C_1$-$C_4$)alkoxycarbonyl radical, a ($C_1$-$C_4$)alkoxycarbonyl radical, a $C_1$-$C_4$ alkoxy radical, a sulphonic radical —$SO_3H$.

Preferably $R_2$ and $R_5$ represent, independently of one another:

a hydrogen atom, a hydroxyl radical, a $C_1$-$C_4$ alkyl radical which can be functionalized with a ($C_1$-$C_4$)alkoxycarbonyl radical, a ($C_1$-$C_4$)alkoxycarbonyl radical, a $C_1$-$C_4$ alkoxy radical.

Another particular embodiment of the invention relates to 1,8-dihydroxynaphthalene derivatives of formula (I) for which $R_3$ and $R_4$ represent a hydrogen atom.

More particularly, the compounds according to the invention are chosen from those below:

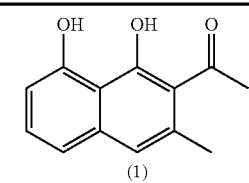

(1) 1-(1,8-Dihydroxy-3-methylnaphthalen-2-yl)ethanone

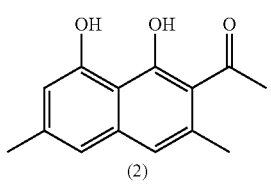

(2) 1-(1,8-Dihydroxy-3,6-dimethylnaphthalen-2-yl)-ethanone

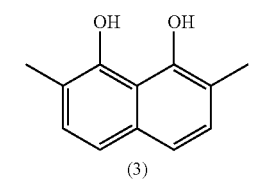

(3) 2,7-Dimethylnaphthalene-1,8-diol

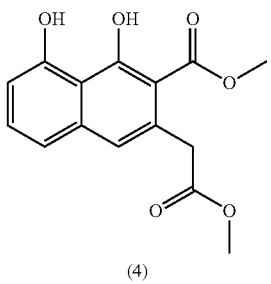

(4) 1,8-Dihydroxy-3-methoxycarbonyl-methylnaphthalene-2-carboxylic acid methyl ester

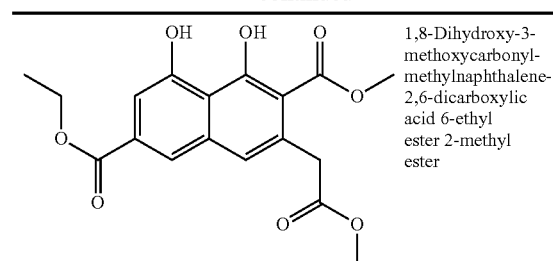

(5) 1,8-Dihydroxy-3-methoxycarbonyl-methylnaphthalene-2,6-dicarboxylic acid 6-ethyl ester 2-methyl ester

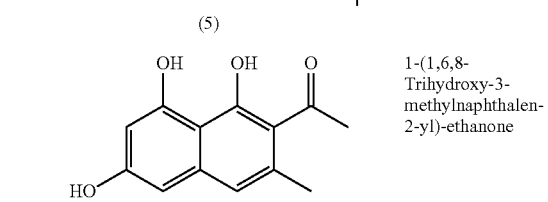

(6) 1-(1,6,8-Trihydroxy-3-methylnaphthalen-2-yl)-ethanone

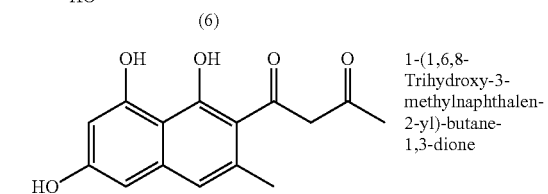

(7) 1-(1,6,8-Trihydroxy-3-methylnaphthalen-2-yl)-butane-1,3-dione

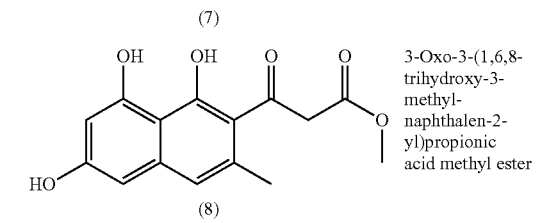

(8) 3-Oxo-3-(1,6,8-trihydroxy-3-methyl-naphthalen-2-yl)propionic acid methyl ester

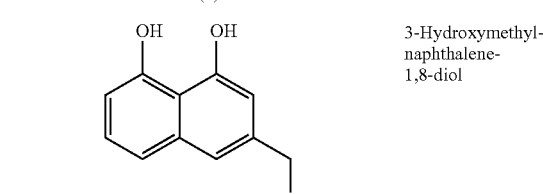

(9) 3-Hydroxymethyl-naphthalene-1,8-diol

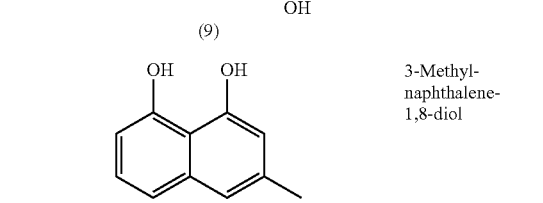

(10) 3-Methyl-naphthalene-1,8-diol

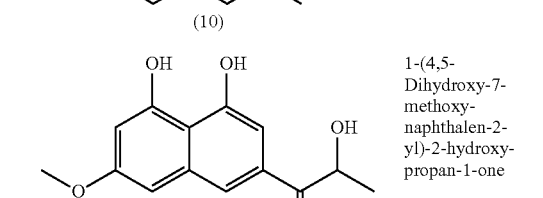

(11) 1-(4,5-Dihydroxy-7-methoxy-naphthalen-2-yl)-2-hydroxy-propan-1-one

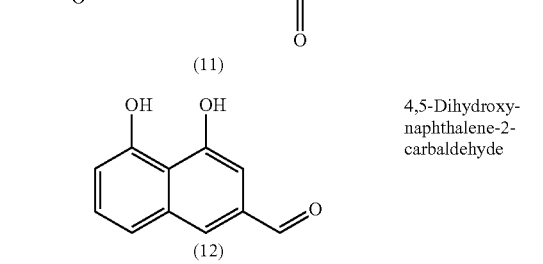

(12) 4,5-Dihydroxy-naphthalene-2-carbaldehyde

-continued

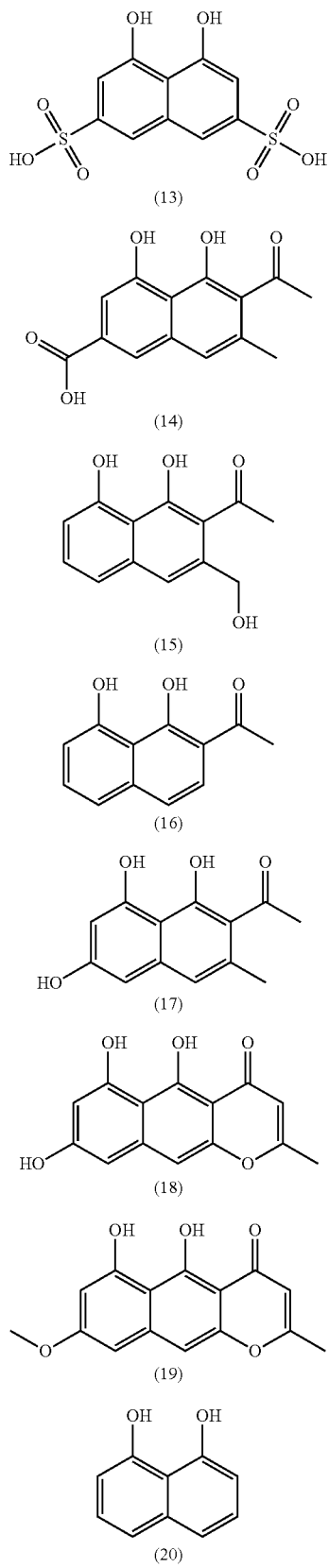

| Structure | Name |
|---|---|
| (13) | 4,5-Dihydroxy-naphthalene-2,7-disulphonic acid |
| (14) | 6-Acetyl-4,5-dihydroxy-7-methylnaphthalene-2-carboxylic acid |
| (15) | 1-(1,8-Dihydroxy-3-hydroxy-methylnaphthalen-2-yl)ethanone |
| (16) | 1-(1,8-Dihydroxy-naphthalen-2-yl)ethanone |
| (17) | 1-(1,6,8-Trihydroxy-3-methyl-naphthalen-2-yl)ethanone |
| (18) | 5,6,8-Trihydroxy-2-methyl-benzo[g]chromen-4-one |
| (19) | 5,6-Dihydroxy-8-methoxy-2-methyl-benzo[g]chromen-4-one |
| (20) | Naphthalene-1,8-diol |

Compounds (1) to (20) and also their optical isomers, geometric isomers, their tautomers, their hydrates and their addition salts with an organic or inorganic base.

The preferred compounds of formula (I) are the compounds (1), (2), (3), (4), (5), (6), (7), (8), (10), (13) and (20).

The 1,8-dihydroxynaphthalene derivatives of formula (I) used in the invention may be natural, synthetic and/or commercially available. The compounds of formula (1) can be synthesized by means of the synthesis pathways described in the literature. In this respect, mention may in particular be made of the references below:

*Journal of Physical Chemistry* A 2007, 111 (2), 345-351,
*Journal of Organic Chemistry* 1990, 55(5), 1611-1623,
*Journal of the Chemical Society, Chemical Communication* 1979, 206, 206,
*Journal of the Chemical Society, Chemical Communication* 1979, 206, 1165,
*Australian Journal of Chemistry* 1988, 41(7), 1087,
*Journal of American Chemical Society* 1988, 110(18), 6172,
*Synthetic Communication* 2007, 37(18), 3041.

The salts of 1,8-dihydroxynaphthalene derivatives of formula (I) according to the invention can be salts of acids or of bases. The acids may be inorganic or organic. Preferably, the acid is hydrochloric acid, which results in chlorides.

The bases can be inorganic or organic. In particular, the bases are alkali metal hydroxides, such as sodium hydroxide, which results in sodium salts.

According to one particular embodiment of the invention, the composition comprises one or more synthetic 1,8-dihydroxynaphthalene derivative(s) of formula (I) which do (does) not exist naturally.

According to another preferred embodiment of the invention, the 1,8-dihydroxynaphthalene derivative(s) of formula (I) according to the invention is (are) natural.

According to one embodiment, the natural 1,8-dihydroxynaphthalene derivatives of formula (I) are derived from extracts of animals, of bacteria, of fungi, of algae or of plants used in their entirety or partially. Preferably, the natural 1,8-dihydroxynaphthalene derivative(s) of formula (I) is (are) derived from a fungus such as *Daldinia concentrica* or from a fruit such as *Diospyros mollis*. These natural 1,8-dihydroxynaphthalene derivatives of formula (I) are obtained from extracts, the purification of which can be carried out by simple extraction without chemical treatment or chemical reaction.

Mixtures of extracts can also be used.

According to one preferred embodiment, the 1,8-dihydroxynaphthalene derivative(s) of formula (I) is (are) solely a natural extract or natural extracts.

The natural extracts according to the invention can be in the form of powers or liquids. The extracts of the invention are preferably in the form of powders.

According to the invention, the synthetic and/or natural 1,8-dihydroxynaphthalene derivative(s) of formula (I) and/or the natural extract(s) used in the composition according to the invention preferably represent(s) from 0.001% to 20% by weight of the total weight of the composition(s) containing the 1,8-dihydroxynaphthalene derivative(s) of formula (I) or the extract(s).

As regards the pure 1,8-dihydroxynaphthalene derivatives of formula (I), the content in the composition(s) containing them is preferably between 0.001% and 20% by weight of each of these compositions.

As regards the extracts, the content in the composition(s) containing the extracts as they are is preferably between 0.001% and 20% by weight of each of these compositions.

Cosmetic Composition:

The cosmetic composition according to the invention is cosmetically acceptable for dyeing keratin fibres, i.e. it comprises a dyeing support which generally contains water or a mixture of water and one or more organic solvents or a mixture of organic solvents.

The term "organic solvent" is intended to mean an organic substance capable of dissolving or dispersing another substance without chemically modifying it.

Organic Solvents:

By way of organic solvent, mention may, for example, be made of $C_1$-$C_4$ lower alkanols, such as ethanol and isopropanol; polyols and polyol ethers, for instance 2-butoxy-ethanol, propylene glycol, propylene glycol monomethyl ether, diethylene glycol monoethyl ether, diethylene glycol monomethyl ether, hexylene glycol; and also aromatic alcohols, for instance benzyl alcohol or phenoxyethanol.

The organic solvents are present in proportions of preferably between 1% and 40% by weight approximately, relative to the total weight of the dyeing composition, and even more preferably between 5% and 30% by weight approximately.

Adjuvants:

The composition(s) of the dyeing process in accordance with the invention can also contain various adjuvants conventionally used in compositions for dyeing the hair, such as anionic, cationic, non-ionic, amphoteric or zwitterionic surfactants or mixtures thereof, anionic, cationic, non-ionic, amphoteric or zwitterionic polymers or blends thereof, inorganic or organic thickeners, and in particular anionic, cationic, non-ionic and amphoteric polymeric associative thickeners, antioxidants, penetration agents, sequestering agents, fragrances, buffers, dispersing agents, conditioning agents such as, for example, modified or non-modified, volatile or non-volatile silicones, film-forming agents, ceramides, preservatives or opacifiers.

Said adjuvants are preferably chosen from surfactants, such as anionic or non-ionic surfactants or mixtures thereof, and inorganic or organic thickeners.

The above adjuvants are, in general, present in an amount, for each of them, of between 0.01% and 40% by weight, relative to the weight of the composition, preferably between 0.1% and 20% by weight, relative to the weight of the composition.

Of course, those skilled in the art will take care to select this or these optional additional compound(s) in such a way that the advantageous properties intrinsically associated with the composition in accordance with the invention are not, or are not substantially, impaired by the addition(s) envisaged.

Additional Dyes:

The composition comprising one or more 1,8-dihydroxynaphthalene derivatives of formula (I) as defined above can also comprise one or more additional direct dyes. These direct dyes are, for example, chosen from those conventionally used in direct dyeing, and among which mention may be made of all the aromatic and/or non-aromatic dyes commonly used, such as neutral, acidic or cationic nitrobenzene direct dyes, neutral, acidic or cationic azo direct dyes, natural direct dyes other than the 1,8-dihydroxynaphthalene derivatives of formula (I), neutral, acidic or cationic quinone, and in particular anthraquinone, direct dyes, azine, triarylmethane and indoamine direct dyes, methines, styryls, porphyrins, metalloporphyrins, phthalocyanines, methinecyanines, and fluorescent dyes. All these additional dyes are different from the 1,8-dihydroxynaphthalene derivatives of formula (I) according to the invention.

Among natural direct dyes, mention may be made of lawsone, juglone, indigo, isatin, curcumin, spinulosin, apigenidine or orceins. Use may also be made of extracts or decoctions containing these natural dyes, and in particular cataplasms or extracts based on henna.

The additional direct dye(s) used in the composition preferably represent(s) from 0.001% to 10% by weight approximately of the total weight of the composition(s) containing them, and even more preferably from 0.05% to 5% by weight approximately.

The cosmetic composition according to the invention comprising one or more 1,8-dihydroxynaphthalene derivatives of formula (I) as defined above can also employ or comprise one or more oxidation bases and/or one or more couplers conventionally used for dyeing keratin fibres.

Among the oxidation bases, mention may be made of para-pheneylenediamines, bisphenylalkylenediamines, para-aminophenols, bis-para-aminophenols, ortho-amino-phenols, heterocyclic bases, and their addition salts.

Among these couplers, mention may in particular be made of meta-phenylenediamines, meta-aminophenols, meta-diphenols, naphthalene couplers, heterocyclic couplers, and their addition salts.

The oxidation base(s) present in the composition(s) is (are) in general each present in an amount of between 0.001% and 10% by weight of the total weight of the corresponding composition(s).

According to another particular embodiment of the invention, the composition according to the invention contains no oxidation base.

According to yet another embodiment, the composition contains no coupler. Preferably, the composition according to the invention contains no oxidation base or couplers especially of aromatic amine type.

According to yet another embodiment, the composition of the invention contains neither dihydroxyindole nor dihydroxyindoline derivatives especially neither 5,6-dihydroxyindole nor 5,6-dihydroxyindoline.

According to another embodiment, the composition contains dihydroxyindole and/or dihydroxyindoline derivatives especially 5,6-dihydroxyindole and/or 5,6-dihydroxyindoline.

The cosmetic composition of the invention can be in various galenical forms, such as a powder, a lotion, a foam, a cream or a gel, or in any other appropriate form for carrying out dyeing of keratin fibres. It can also be packaged in a propellant-free pump-dispenser or under pressure in an aerosol container in the presence of a propellant and form a foam.

pH of the Composition

According to one particular embodiment of the invention, the pH of the composition containing the 1,8-dihydroxynaphthalene derivative(s) of formula (I) is greater than 7, and preferably between 8 and 12. It is in particular between 9 and 11.

The pH of the composition according to the invention can be adjusted to the desired value by means of acidifying or basifying agents conventionally used in the dyeing of keratin fibres, or else using conventional buffer systems.

Among the acidifying agents of the compositions used in the invention, mention may be made, by way of example, of inorganic or organic acids such as hydrochloric acid, orthophosphoric acid or sulphuric acid, carboxylic acids such as acetic acid, tartaric acid, citric acid or lactic acid, and sulphonic acids.

Basifying Agents

The composition according to the invention contains one or more basifying agent(s) other than aqueous ammonia.

The amount of the basifying agent(s) is preferably such that the pH of the composition is between 8 and 12. It is more particularly between 9 and 11.

The basifying agent other than aqueous ammonia is preferably chosen from alkanolamines such as mono-, di- and triethanolamines, alkali metal carbonate salts, guanidine, imidazole, sodium hydroxide, potassium hydroxide or calcium hydroxide, and arginine and the compounds of formula (II) below:

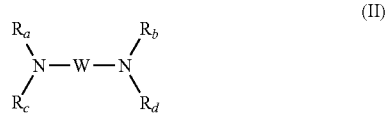

in which formula (II):
W is a $(C_1$-$C_{10})$alkylene radical optionally interrupted by one or more heteroatoms such as oxygen atom, or by one or more groups NR wherein R represents an hydrogen atom, or (hydroxyl)$(C_1$-$C_6)$alkyl group, the said alkylene radical is optionally substituted by one or more hydroxyl or $(C_1$-$C_4)$alkyl group;
W represents especially a propylene radical optionally substituted by a hydroxyl group or a $C_1$-$C_4$ alkyl radical;
$R_a$, $R_b$, $R_c$ and $R_d$, which may be identical or different, represent a hydrogen atom, a $C_1$-$C_4$ alkyl radical or a $C_1$-$C_4$ hydroxyalkyl radical.

More particularly, the basifying agent(s) is (are) chosen from ethanolamine, carbonate salts, guanidine, imidazole, calcium hydroxide and arginine.

Oxidizing Agents and Oxidation Catalysts

According to one particular embodiment of the invention, the composition contains a chemical oxidizing agent. The term "chemical oxidizing agent" is intended to mean an oxidizing agent other than oxygen in the air ($O_2$), such as hydrogen peroxide, urea peroxide, alkali metal bromates, persalts such as perborates and persulphates, or several hydrogen peroxide-generating system(s) such as:
  polymeric complexes which can release hydrogen peroxide, such as polyvinylpyrrolidone/$H_2O_2$, in particular in the form of powders, and the other polymeric complexes described in U.S. Pat. No. 5,008,093; U.S. Pat. No. 3,376,110; U.S. Pat. No. 5,183,901;
  metal peroxides which, in water, generate hydrogen peroxide, such as calcium peroxide or magnesium peroxide;
  oxidases which produce hydrogen peroxide in the presence of a suitable substrate (for example, glucose in the case of glucose oxidase or uric acid with uricase); and also enzymes, among which mention may be made of peroxidases, 2-electron oxidoreductases, such as uricases, and 4-electron oxygenases such as laccases.

The use of hydrogen peroxide is particularly preferred.

In particular, the chemical oxidizing agent is present in the composition in proportions of between 0.001% and 12%, relative to the total weight of the composition.

According to another particular embodiment of the invention, the composition contains no chemical oxidizing agent. The oxidation and the appearance of the colour then takes place only with oxygen in the air.

According to another variant, the composition also contains an oxidation catalyst. By way of example, this catalyst can be chosen from manganese (Mn) salts, zinc (Zn) salts, iron (Fe) salts and copper (Cu) salts. In particular, the catalysts are present in the composition in proportions of between 0.001% and 10%, relative to the total weight of the composition.

Mordants

The composition according to the invention can also contain a mordant or mordanting agent which is conventionally used in the textile industry and which is cosmetically acceptable, preferably in the form of metal salts, such as iron salts, aluminium salts, titanium salts, calcium salts, manganese salts, copper salts, zinc salts or strontium salts. By way of example, the mordant may be iron sulphate, manganese gluconate, copper sulphate, zinc gluconate, calcium chloride, magnesium chloride, potassium titanyl oxalate or strontium acetate. In particular, the mordants are present in the composition in proportions of between 0.001% and 10%, relative to the total weight of the composition.

Dyeing Process in One or More Steps

A subject of the invention relates to the process for dyeing by treatment of the keratin fibres with or application to the keratin fibres of i) one or more 1,8-dihydroxynaphthalene derivatives of formula (I) as defined above and ii) one or more basifying agent(s) other than aqueous ammonia, it being possible for the ingredient(s) i) and ii) to be applied to the fibres either simultaneously in one step, or successively in several steps.

According to one preferred embodiment of the dyeing process of the invention, the ingredients i) and ii) are applied in one step. In which case, preferably, the ingredients i) and ii) are together in one cosmetic composition, which is then applied to the keratin fibres.

According to another particular embodiment of the dyeing process of the invention, the ingredients i) and ii) are applied successively. In which case, preferably, the ingredient i) is in one cosmetic composition and the ingredient ii) is in another cosmetic composition. According to a first advantageous variant of the invention, the cosmetic composition comprising the ingredient i) is applied to the keratin fibres in a first step, and then, in a second step, a cosmetic composition comprising the ingredient ii) is applied. According to another variant of the invention, the cosmetic composition comprising the ingredient ii) is applied to the keratin fibres in a first step, and then, in a second step, a cosmetic composition comprising the ingredient i) is applied.

According to one preferred embodiment of the process according to the invention, the process uses neither oxidation bases nor couplers. More particularly, the process does not involve an oxidation base or a coupler of aromatic amine type.

According to another preferred embodiment of the dyeing process, the composition applied to the keratin fibres which contains a basifying agent other than aqueous ammonia that does not have an unpleasant odour is chosen from alkanolamines, such as mono-, di- and triethanolamines, alkali metal carbonate salts, guanidine, imidazole, sodium hydroxide, potassium hydroxide or calcium hydroxide and arginine and the compounds of formula (II) as defined above. More particularly, the basifying agent(s) which does not (do not) have an unpleasant odour is (are) chosen from ethanolamine, carbonate salts, guanidine, imidazole, calcium hydroxide and arginine.

Preferably, the basifying agent other than aqueous ammonia is present in an amount such that the pH is between 8 and 12. It is more particularly between 9 and 11.

A variant of the invention relates to the dyeing process which involves one or more chemical oxidizing agent(s) as defined above. This oxidizing agent(s) can be applied to the fibres simultaneously with the ingredient i) and ii) or in an additional step. Preferably, the chemical oxidizing agent(s) is (are) applied together with the ingredients i) and ii). In this case, the ingredients i) and ii) and the chemical oxidizing agent(s) are preferably in the same cosmetic composition and are applied to the keratin fibres in a single step. According to this particular process of the invention, the composition applied to the fibres contains the 1,8-dihydroxynaphthalene derivatives of formula (I), also contains one or more basifying agent(s) other than aqueous ammonia and its derivative(s), and additionally contains one or more chemical oxidizing agent(s).

Preferably, the chemical oxidizing agent is present in a proportion of between 0.001% and 12%, relative to the total weight of the composition comprising the ingredients i) and ii).

More particularly, the chemical oxidizing agent(s) is (are) hydrogen peroxide.

According to another preferred variant of the process of the invention, the oxidation is carried out with oxygen in the air in the absence of any chemical oxidizing agent. In other words, no step of the dyeing process involves an oxidizing agent other than oxygen in the air.

According to a preferred dyeing process of the invention, the cosmetic composition is applied in a single step and contains one or more 1,8-dihydroxynaphthalene derivative(s) of formula (I), also contains one or more basifying agent(s) other than aqueous ammonia, and contains no chemical oxidizing agent, the dyeing taking place only with oxygen in the art.

According to another preferred embodiment of the dyeing process, the composition containing the ingredient i), i.e. the 1,8-dihydroxynaphthalene derivative(s) of formula (I) as defined above, also contains an oxidation catalyst. By way of example, this catalyst can be manganese gluconate or zinc gluconate.

The leave-in time for the oxidation to be carried out in the air is between 3 and 120 minutes. Preferably, after application of the composition containing the 1,8-dihydroxynaphthalene derivatives of formula (I), the composition is left to act for 10 to 60 minutes.

The application can be carried out in one or more steps, under oxidizing and basic conditions.

According to another embodiment, the dyeing process according to the invention is carried out dihydroxyindole and/or dihydroxyindoline derivatives especially 5,6-dihydroxyindole and/or 5,6-dihydroxyindoline.

According to yet another embodiment, the dyeing process according to the invention is carried out neither dihydroxyindole nor dihydroxyindoline derivatives especially neither 5,6-dihydroxyindole nor 5,6-dihydroxyindoline.

According to another particular embodiment of the dyeing process, the composition containing the ingredient i), i.e. the 1,8-dihydroxynaphthalene derivative(s) of formula (I), also contains one or more mordant(s) conventionally used. This treatment is particularly carried out before the application of the composition according to the invention comprising the 1,8-dihydroxynaphthalene derivative(s) of formula (I) as defined above, or after the dyeing process. By way of example, the mordant may be iron sulphate.

A particular variant of the invention consists of a dyeing process in which the keratin fibres are treated with the ingredient i) one or more 1,8-dihydroxynaphthalene derivative(s) of formula (I) as defined above; the ingredient ii) one or more basifying agent(s) other than aqueous ammonia; optionally, the ingredient iii) one or more oxidizing agents; optionally the ingredient iv) one or more oxidation catalyst(s); and, optionally, the ingredient v) one or more mordants, in different steps.

The leave-in time after application of the composition according to the invention comprising the 1,8-dihydroxynaphthalene derivative(s) of formula (I) as defined above, and between each step of treatment with the basifying agent(s), with, optionally, the oxidation catalyst(s) and with, optionally, the mordant(s), is set at between 3 and 120 minutes, preferably between 10 and 60 minutes, and more particularly between 15 and 45 minutes.

Whatever the method of application, the application temperature is generally between ambient temperature and 80° C., and more particularly between 15° C. and 45° C. Thus, it is advantageously possible, after application of the composition(s) comprising the ingredients i) to v) as defined above, to subject the head of hair to a heat treatment by heating at a temperature of between 30 and 60° C. In practice, this operation can be carried out by means of a hairdressing hood, a hairdryer, an infrared ray dispenser and other conventional heating devices.

It is possible to use, both as means for heating and means for smoothing out the head of hair, a heating iron at a temperature of between 60 and 220° C., preferably between 120 and 200° C.

One particular embodiment of the invention relates to a dyeing process which is carried out at ambient temperature (25° C.).

After application of the ingredients i) to v) as defined above, to the keratin fibres, said locks are preferably rinsed with water, washed with conventional shampoo and dried by means such as have been described above.

According to a particular dyeing process of the invention, the composition comprising the ingredients i) to ii) is applied to the keratin fibres, particularly the hair, in one step, and is then left in for between 15 and 60 minutes, preferably 30 minutes, and then said fibres are rinsed with water, washed with conventional shampoo and dried.

In all the particular embodiments and variants of the processes described above, the compositions mentioned are ready-to-use compositions which can result from the extemporaneous mixing of two or more compositions, and in particular of compositions present in dyeing kits.

iv) Dyeing device or "kit":

Another subject of the invention is a multicompartment dyeing device or dyeing "kit". Advantageously, this device comprises from 2 to 5 compartments containing from 2 to 5 compositions, in which the following ingredients are distributed:

i) one or more 1,8-dihydroxynaphthalene derivative(s) of formula (I) as defined above,
ii) one or more basifying agent(s) as defined above,
iii) optionally, one or more chemical oxidizing agent(s) and/or iv) one or more oxidation catalyst(s), and
v) optionally, one or more mordant(s).

The compositions of the device according to the invention are packaged in distinct compartments, optionally accompanied by suitable application means, which may be identical or different, such as paint brushes, brushes or sponges.

The device mentioned above can also be equipped with a means for delivering the desired mixture onto the hair, for example such as the devices described in patent FR 2 586 913.

DYEING EXAMPLES

The compounds (1) and (20) are commercially available. The compound (2) can be obtained using a synthesis pathway described in *Journal of Physical Chemistry A*, 2007 111 (2), 345-351.

A) Aqueous Hydrogen Eroxide Solution ($H_2O_2$) Sodium h &Oxide (NaOH) Protocol:

Added to a mixture containing i) 300 mg of compound of formula (I) in 4 ml of water and 4 ml of ethanol are ii) 1 ml of sodium hydroxide at 0.01 mol/l and then iii) 1 ml of 6% aqueous hydrogen peroxide solution. This composition is applied to a lock of 0.5 g of natural hair containing 90% white hairs. The preparation is left in for 30 minutes at ambient temperature, and then the lock is rinsed with water, washed with shampoo and dried.

Visual and Olfactory Dyeing Results of the $H_2O_2$+NaOH Protocol:

The following results were obtained:

| Compound of formula (I) | Colour | Unpleasant odour |
|---|---|---|
| 1-(1,8-Dihydroxy-3-methylnaphthalen-2-yl)ethanone (1) | Dark brown | None |
| 1-(1,8-Dihydroxy-3,6-dimethylnaphthalen-2-yl)ethanone (2) | Pinky-beige | None |

Despite the absence of aqueous ammonia the hair is coloured in a powerful, chromatic and strong manner without there being any unpleasant odour to deplore during the dyeing. Moreover, it should be noted that the cosmetic aspect of the fibres is respected (feel to the touch).

B) Oxygen in the Air ($O_2$)+NaOH Protocol:

Added to a mixture containing i) 300 mg of compound of formula (I) in 4 ml of water and 4 ml of ethanol are ii) 2 ml of sodium hydroxide at 0.01 mol/l.

This solution is applied to a lock of 0.5 g of natural hair containing 90% white hairs. The preparation is oxidized with iii) oxygen in the air for 30 minutes, and then the lock is rinsed with water, washed with shampoo and dried.

Visual and Olfactory Dyeing Results of the $O_2$+NaOH Protocol:

The following results are obtained:

| Compound of formula (I) | Colour | Unpleasant odour |
|---|---|---|
| 1-(1,8-Dihydroxy-3-methylnaphthalen-2-yl)ethanone (1) | Yellow | None |
| 1-(1,8-Dihydroxy-3,6-dimethylnaphthalen-2-yl)ethanone (2) | Pinkish | None |

Despite the absence of aqueous ammonia and of chemical oxidizing agent, the hair is coloured in a chromatic manner. Moreover, during the treatment of the hair, no unpleasant odour was present. It should also be noted that the cosmetic aspect of the fibre is respected (feel to the touch).

C) Oxygen in the Air+Potassium Carbonate ($K_2CO_3$) Protocol:

Added to a mixture containing i) 75 mg of compound of formula (I) in 1.75 ml of water and 0.75 ml of ethanol is ii) potassium carbonate so as to reach a pH of 10.7. This solution is applied to a lock of 0.5 g of natural hair containing 90% white hairs. The preparation is oxidized with oxygen in the air for 30 minutes, and then the lock is rinsed with water, washed with shampoo and dried.

Visual and Results of the $O_2$+$K_2CO_3$ Protocol:

The following results are obtained:

| Compound of formula (I) | Colour | Unpleasant odour |
|---|---|---|
| 1-(1,8-Dihydroxy-3-methylnaphthalen-2-yl)ethanone (1) | Orange | None |
| 1-(1,8-Dihydroxy-3,6-dimethylnaphthalen-2-yl)ethanone (2) | Orangey-yellow | None |
| 1,8-Dihydroxynaphthalene (20) | Brown | None |

Despite the absence of aqueous ammonia and of chemical oxidizing agent, the hair is coloured in a chromatic manner. Moreover, during the treatment of the hair, no unpleasant odour was present. It should also be noted that the cosmetic aspect of the fibre is respected (feel to the touch).

D) Oxygen in the Air+Monoethanolamine (MEA) Protocol:

Added to a mixture containing i) 75 mg of compound of formula (I) in 1.75 ml of water and 0.75 ml of ethanol is ii) monoethanolamine so as to reach a pH of 9.5. This solution is applied to a lock of 0.5 g of natural hair containing 90% white hairs. The preparation is oxidized with oxygen in the air for 30 minutes, and then the lock is rinsed with water, washed with shampoo and dried.

Visual and Olfactory Dyeing Results of the $O_2$+MEA Protocol:

The following results were obtained:

| Compound of formula (I) | Colour | Unpleasant odour |
|---|---|---|
| 1,8-Dihydroxynaphthalene (20) | Reddish-brown | None |

Despite the absence of aqueous ammonia and of a chemical oxidizing agent, the hair is coloured in a chromatic manner. Moreover, during the treatment of the hair, no unpleasant odour is present. It should also be noted that the cosmetic aspect of the fibre is respected (feel to the touch).

E) Comparative According to Prior Art (WO 94/18937)

1,8-Dihydroxynaphthalene Compound (20) with Air+Aqueous Ammonia

Added to a mixture containing i) 75 mg of compound of formula (I) in 1.75 ml of water and 0.75 ml of ethanol is ii) aqueous ammonia so as to reach a pH of 9.5.

This solution is applied to a lock of 0.5 g of natural hair containing 90% white hairs. The preparation is oxidized with oxygen in the air for 30 minutes, and then the lock is rinsed with water, washed with shampoo and dried.

Visual and Results of the $O_2$+$NH_3$ Protocol:

The following results were obtained:

| Compound | Colour | Unpleasant odour |
|---|---|---|
| 1,8-Dihydroxynaphthalene (20) | Pale orange | Yes |

Unlike protocols C and D according to the invention, and despite the presence of aqueous ammonia, the hair is barely coloured. Moreover, during the treatment of the hair, an unpleasant odour is present, unlike processes C and D according to the invention, where there is no unpleasant odour to be deplored.

The invention claimed is:

1. A process for dyeing keratin fibres, comprising treating the fibres with:

i) at least one 1,8-dihydroxynaphthalene derivative of formula (I):

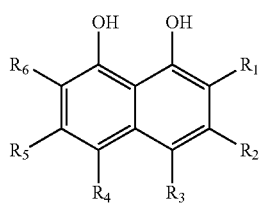

(I)

inorganic or organic acids or bases, optical isomers, geometric isomers, tautomers, and/or solvates thereof, wherein:
  $R_1$ and $R_6$ are, independently of one another, chosen from:
    hydrogen atoms,
    $C_1$-$C_4$ alkyl radicals which can be functionalized with at least one hydroxyl or $(C_1$-$C_4)$alkoxycarbonyl radical,
    carboxylic radicals —$CO_2H$,
    $(C_1$-$C_4)$alkoxycarbonyl radicals,
    $(C_1$-$C_4)$alkylcarbonyl radical which can be functionalized with a $(C_1$-$C_4)$alkylcarbonyl radical or a $(C_1$-$C_4)$ alkoxycarbonyl radical,
    $C_1$-$C_4$ alkoxy radicals,
    carboxaldehyde radicals —CHO, and
    sulphonic radicals —$SO_3H$;
  $R_2$ and $R_5$ are, independently of one another, chosen from:
    hydrogen atoms,
    hydroxyl radicals,
    $C_1$-$C_4$ alkyl radicals which can be functionalized with at least one hydroxyl or $(C_1$-$C_4)$alkoxycarbonyl radical,
    carboxylic radicals —$CO_2H$,
    $(C_1$-$C_4)$alkoxycarbonyl radicals,
    $(C_1$-$C_4)$alkylcarbonyl radicals which can be functionalized with a hydroxyl radical,
    carboxaldehyde radicals —CHO, and
    sulphonic radicals —$SO_3H$;
  $R_3$ and $R_4$ are, independently of one another, chosen from:
    hydrogen atoms,
    hydroxyl radicals,
    $C_1$-$C_4$ alkyl radicals which can be functionalized with at least one hydroxyl and $(C_1$-$C_4)$alkoxycarbonyl radical,
    carboxylic radicals —$CO_2H$,
    $(C_1$-$C_4)$alkoxycarbonyl radicals, and
    $(C_1$-$C_4)$alkylcarbonyl radicals which can be functionalized with a $(C_1$-$C_4)$alkylcarbonyl radical or a $(C_1$-$C_4)$ alkoxycarbonyl radical;
  $R_1$ and $R_2$ can form, together with the carbon atoms to which they are attached, a heterocycle optionally substituted with an oxo group, optionally functionalized with one or two $C_1$-$C_4$ alkyl radicals:

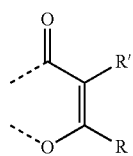

with R and R', which may be identical or different, representing a hydrogen atom or a $C_1$-$C_4$ alkyl radical;
and
ii) at least one basifying agent other than aqueous ammonia;

wherein:
  the at least one 1,8-dihydroxynaphthalene derivative of formula (I) and the at least one basifying agent can be applied simultaneously or successively to the keratin fibers, and
  wherein the dyeing process does not involve aqueous ammonia.

2. The process according to claim 1, wherein R and R' represent a hydrogen atom or a R' represents a hydrogen atom and R represents a $C_1$-$C_4$ alkyl radical.

3. The process according to claim 1, wherein $R_1$ and $R_2$ can form, together with the carbon atoms to which they are attached, 4-pyrone.

4. The process according to claim 1, wherein the at least one 1,8-dihydroxynaphthalene derivative of formula (I) is chosen such that $R_1$ and $R_6$ are, independently of one another, chosen from:
  hydrogen atoms,
  $C_1$-$C_4$ alkyl radicals,
  carboxylic radicals —$CO_2H$,
  $(C_2$-$C_4)$alkoxycarbonyl radicals, and
  $(C_1$-$C_4)$alkylcarbonyl radicals which can be functionalized with a $(C_1$-$C_4)$alkylcarbonyl radical or a$(C_1$-$C_4)$alkoxycarbonyl radical.

5. The process according to claim 1, wherein the at least one 1,8-dihydroxynaphthalene derivative of formula (I) is chosen such that $R_3$ and $R_4$ represent a hydrogen atom.

6. The process according to claim 1, wherein the at least one 1,8-dihydroxynaphthalene derivative of formula (I) is chosen such that $R_2$ and $R_5$ are, independently of one another, chosen from:
  hydrogen atoms,
  hydroxyl radicals,
  $C_1$-$C_4$ alkyl radicals which can be functionalized with a $(C_1$-$C_4)$alkoxycarbonyl radical,
  $(C_1$-$C_4)$alkoxycarbonyl radicals,
  $C_1$-$C_4$ alkoxy radicals, and
  sulphonic radicals —$SO_3H$.

7. The process according to claim 1, wherein the at least one 1,8-dihydroxynaphthalene derivative of formula (I) is chosen from the compounds below:

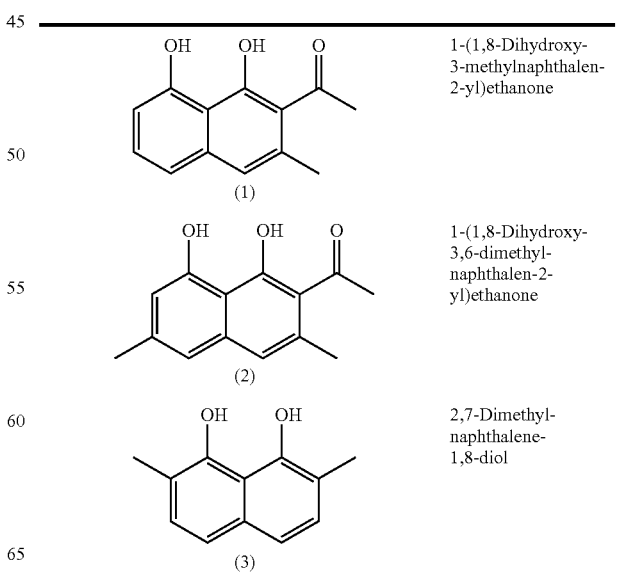

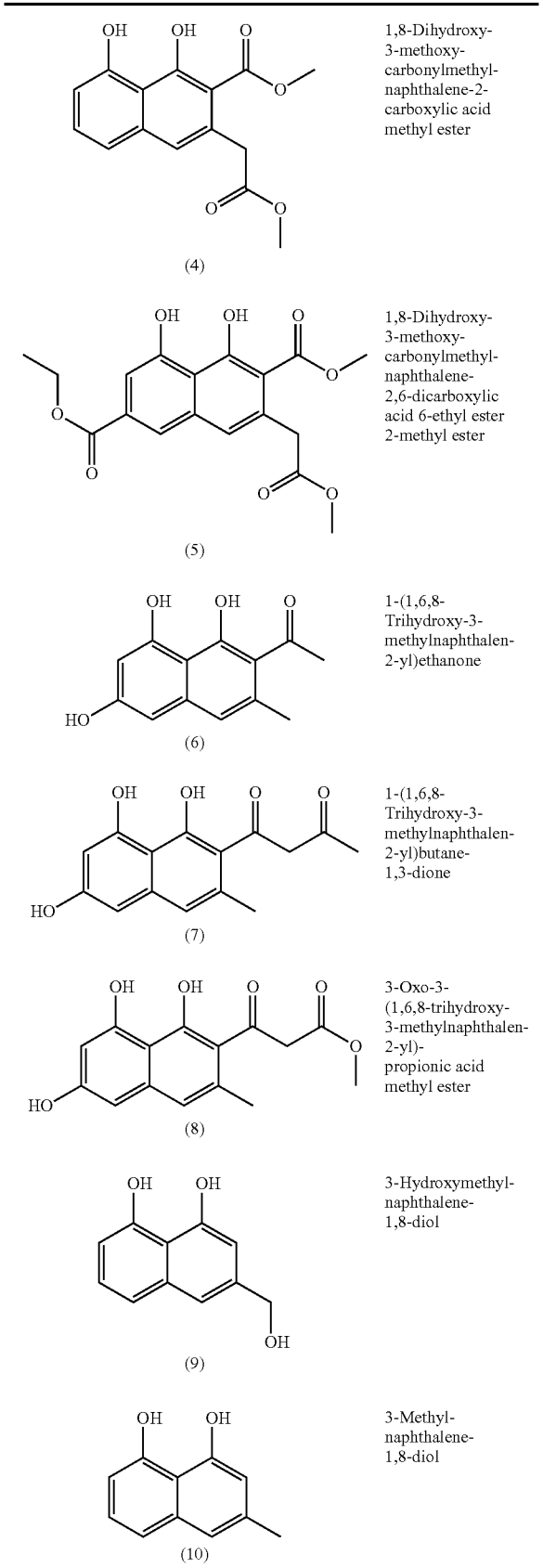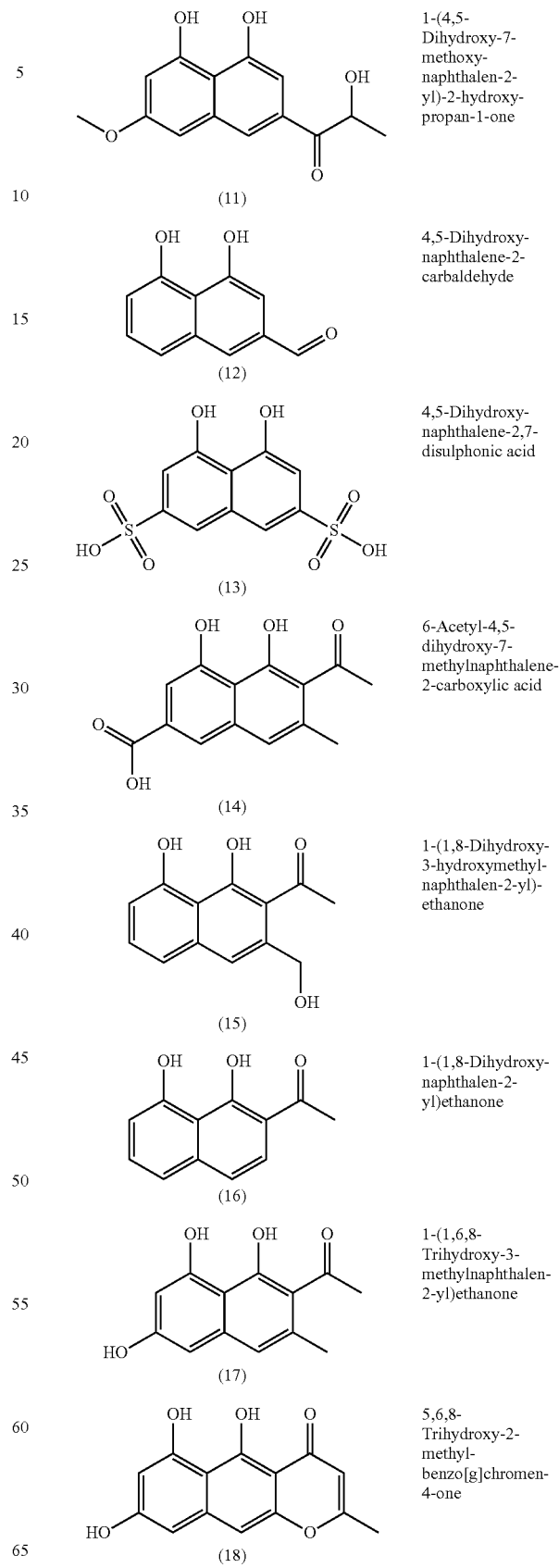

-continued

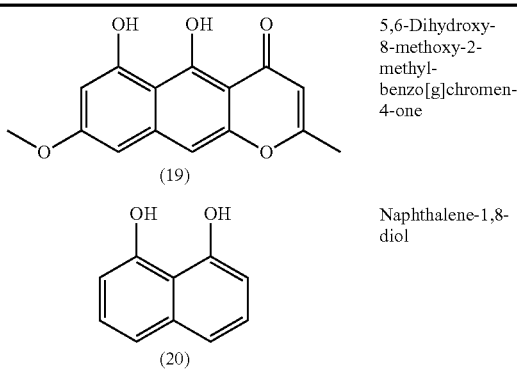

| Structure | Name |
|---|---|
| (19) | 5,6-Dihydroxy-8-methoxy-2-methyl-benzo[g]chromen-4-one |
| (20) | Naphthalene-1,8-diol | and optical isomers, geometric isomers, tautomers, hydrates, and organic or inorganic base addition salts thereof.

8. The process according to claim 7, wherein the at least one 1,8-dihydroxynaphthalene derivative of formula (I) is chosen from the compounds (1), (2), (3), (4), (5), (6), (7), (8), (10), (13) and (20).

9. The process according to claim 1, wherein the at least one 1,8-dihydroxynaphthalene derivative of formula (I) and the at least one basifying agent are present together in a cosmetic composition.

10. The process according to claim 9, wherein the at least one basifying agent is present in an amount such that the pH of the cosmetic composition is between 8 and 12.

11. The process according to claim 1, wherein the at least one basifying agent is chosen from alkanolamines, alkali metal carbonate salts, guanidine, imidazole, sodium hydroxide, potassium hydroxide, calcium hydroxide, arginine, and the compounds of formula (II):

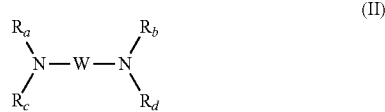

wherein:
W is a $(C_1-C_{10})$alkylene radical optionally interrupted by at least one heteroatom, at least one group NR, wherein R represents an hydrogen atom, or at least one (hydroxyl)$(C_1-C_6)$alkyl group, wherein the alkylene radical is optionally substituted by at least one hydroxyl or $(C_1-C_4)$alkyl group;
$R_a$, $R_b$, $R_c$ and $R_d$, which may be identical or different, are chosen from hydrogen atoms, $C_1-C_4$ alkyl radicals, and $C_1-C_4$ hydroxyalkyl radicals.

12. The process according to claim 11, wherein W represents a propylene radical optionally substituted by a hydroxyl group or a $C_1-C_4$ alkyl radical.

13. The process according to claim 1, further comprising treating the fibers with at least one chemical oxidizing agent other than oxygen in the air:
a) either simultaneously with the at least one 1,8-dihydroxynaphthalene derivative of formula (I) and the at least one basifying agent;
b) or in an additional step.

14. The process according to claim 13, wherein the at least one chemical oxidizing agent is chosen from hydrogen peroxide, urea peroxide, urea peroxide, alkali metal bromates, persalts, and hydrogen peroxide-generating systems.

15. The process according to claim 14, wherein the hydrogen peroxide-generating systems are chosen from polymeric complexes that can release hydrogen peroxide, metal peroxides that, in water, generate hydrogen peroxide, oxidases that produce hydrogen peroxide in the presence of a suitable substrate, and enzymes.

16. The process according to claim 1, wherein there is no chemical oxidizing agent.

17. The process according to claim 1, further comprising the use of at least one oxidation catalyst chosen from manganese salts, zinc salts, iron salts, and copper salts.

18. The process according to claim 1, wherein the process uses no oxidation base or aromatic amine coupler.

19. A cosmetic composition comprising:
i) at least one 1,8-dihydroxynaphthalene derivative of formula (I)

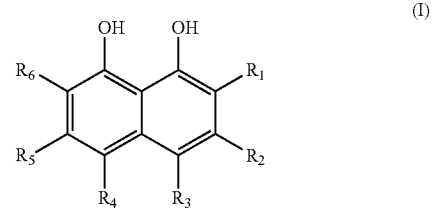

inorganic or organic acids or bases, optical isomers, geometric isomers, tautomers, and/or solvates thereof, wherein:
$R_1$ and $R_6$ are, independently of one another, chosen from:
hydrogen atoms,
$C_1-C_4$ alkyl radicals which can be functionalized with at least one hydroxyl or $(C_1-C_4)$alkoxycarbonyl radical,
carboxylic radicals —$CO_2H$,
$(C_1-C_4)$alkoxycarbonyl radicals,
$(C_1-C_4)$alkylcarbonyl radical which can be functionalized with a $(C_1-C_4)$alkylcarbonyl radical or a $(C_1-C_4)$alkoxycarbonyl radical,
$C_1-C_4$ alkoxy radicals,
carboxaldehyde radicals —CHO, and
sulphonic radicals —$SO_3H$;
$R_2$ and $R_5$ are, independently of one another, chosen from:
hydrogen atoms,
hydroxyl radicals,
$C_1-C_4$ alkyl radicals which can be functionalized with at least one hydroxyl or $(C_1-C_4)$alkoxycarbonyl radical,
carboxylic radicals —$CO_2H$,
$(C_1-C_4)$alkoxycarbonyl radicals,
$(C_1-C_4)$alkylcarbonyl radicals which can be functionalized with a hydroxyl radical,
carboxaldehyde radicals —CHO, and
sulphonic radicals —$SO_3H$;
$R_3$ and $R_4$ are, independently of one another, chosen from:
hydrogen atoms,
hydroxyl radicals,
$C_1-C_4$ alkyl radicals which can be functionalized with at least one hydroxyl and $(C_1-C_4)$alkoxycarbonyl radical,
carboxylic radicals —$CO_2H$,
$(C_1-C_4)$alkoxycarbonyl radicals, and
$(C_1-C_4)$alkylcarbonyl radicals which can be functionalized with a $(C_1-C_4)$alkylcarbonyl radical or a $(C_1-C_4)$alkoxycarbonyl radical;
$R_1$ and $R_2$ can form, together with the carbon atoms to which they are attached, a heterocycle optionally substituted with an oxo group, optionally functionalized with one or two $C_1$-$C_4$ alkyl radicals:

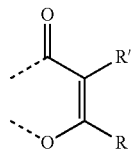

with R and R', which may be identical or different, representing a hydrogen atom or a $C_1$-$C_4$ alkyl radical;

and ii) at least one basifying agent other than aqueous ammonia;

with the proviso that the at least one 1,8-dihydroxynaphthalene derivative of formula (I) does not represent:

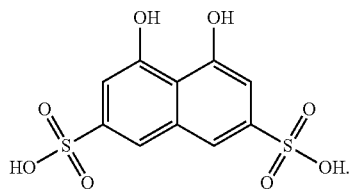 [SMILES: O=S(=O)(O)c1cc(O)c2c(O)cc(S(=O)(=O)O)cc2c1]

20. The cosmetic composition according to claim 19, further comprising at least one chemical oxidizing agent chosen from hydrogen peroxide, urea peroxide, urea peroxide, alkali metal bromates, persalts, and hydrogen peroxide-generating systems.

21. A multicompartment device comprising from 2 to 5 compartments containing from 2 to 5 compositions, wherein ingredients i) through v) are distributed in the compartments:

i) at least one 1,8-dihydroxynaphthalene derivative of formula (I)

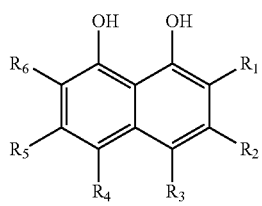

inorganic or organic acids or bases, optical isomers, geometric isomers, tautomers, and/or solvates thereof, wherein:

$R_1$ and $R_6$ are, independently of one another, chosen from:
hydrogen atoms,
$C_1$-$C_4$ alkyl radicals which can be functionalized with at least one hydroxyl or $(C_1$-$C_4)$alkoxycarbonyl radical,
carboxylic radicals —$CO_2H$,
$(C_1$-$C_4)$alkoxycarbonyl radicals,
$(C_1$-$C_4)$alkylcarbonyl radical which can be functionalized with a $(C_1$-$C_4)$alkylcarbonyl radical or a $(C_1$-$C_4)$ alkoxycarbonyl radical,
$C_1$-$C_4$ alkoxy radicals,
carboxaldehyde radicals —CHO, and
sulphonic radicals —$SO_3H$;

$R_2$ and $R_5$ are, independently of one another, chosen from:
hydrogen atoms,
hydroxyl radicals,
$C_1$-$C_4$ alkyl radicals which can be functionalized with at least one hydroxyl or $(C_1$-$C_4)$alkoxycarbonyl radical,
carboxylic radicals —$CO_2H$,
$(C_1$-$C_4)$alkoxycarbonyl radicals,
$(C_1$-$C_4)$alkylcarbonyl radicals which can be functionalized with a hydroxyl radical,
carboxaldehyde radicals —CHO, and
sulphonic radicals —$SO_3H$;

$R_3$ and $R_4$ are, independently of one another, chosen from:
hydrogen atoms,
hydroxyl radicals,
$C_1$-$C_4$ alkyl radicals which can be functionalized with at least one hydroxyl and $(C_1$-$C_4)$alkoxycarbonyl radical,
carboxylic radicals —$CO_2H$,
$(C_1$-$C_4)$alkoxycarbonyl radicals, and
$(C_1$-$C_4)$alkylcarbonyl radicals which can be functionalized with a $(C_1$-$C_4)$alkylcarbonyl radical or a $(C_1$-$C_4)$ alkoxycarbonyl radical;

$R_1$ and $R_2$ can form, together with the carbon atoms to which they are attached, a heterocycle optionally substituted with an oxo group, optionally functionalized with one or two $C_1$-$C_4$ alkyl radicals:

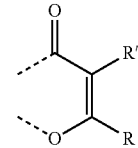

with R and R', which may be identical or different, representing a hydrogen atom or a $C_1$-$C_4$ alkyl radical;

ii) at least one basifying agent other than aqueous ammonia;

iii) optionally, at least one chemical oxidizing agent;

iv) optionally at least one oxidation catalyst; and v) optionally, at least one mordant.

* * * * *